United States Patent [19]

Pellegrini, Jr. et al.

[11] 4,334,113

[45] Jun. 8, 1982

[54] SYNTHETIC HYDROCARBON OLIGOMERS

[75] Inventors: John P. Pellegrini, Jr., O'Hara Township, Allegheny County; David L. Beach; Thaddeus P. Kobylinski, both of Gibsonia, all of Pa.

[73] Assignee: Gulf Research & Development Company, Pittsburgh, Pa.

[21] Appl. No.: 191,867

[22] Filed: Sep. 29, 1980

Related U.S. Application Data

[63] Continuation-in-part of Ser. No. 158,482, Jun. 11, 1980, abandoned.

[51] Int. Cl.³ .............................................. C07C 5/02
[52] U.S. Cl. .................................... 585/18; 585/255; 585/510; 585/530
[58] Field of Search ................... 585/12, 18, 255, 510, 585/530

[56] References Cited

U.S. PATENT DOCUMENTS 3,578,650  5/1971  Mitchell et al. ..................... 585/530
3,814,679  6/1974  Erlmeier et al. ..................... 585/18
3,985,821  10/1976  Girotti et al. ......................... 585/18

*Primary Examiner*—Curtis R. Davis
*Attorney, Agent, or Firm*—Deane E. Keith; Forrest D. Stine; Donald L. Rose

[57] ABSTRACT

A synthetic hydrocarbon fluid is prepared by oligomerizing an olefin reactant in the presence of a catalyst prepared by reacting tungsten hexafluoride and water at a moderate temperature. For example, 1-butene is oligomerized at a temperature of about 40° C. in the presence of a catalyst obtained by reacting tungsten hexafluoride and water in a four to one mol ratio. The liquid oligomer product is then hydrogenated to remove residual unsaturation.

21 Claims, No Drawings

SYNTHETIC HYDROCARBON OLIGOMERS

This application is a continuation-in-part of U.S. Ser. No. 158,482, filed June 11, 1980 and now abandoned.

SUMMARY OF THE INVENTION

1-Olefins, including propylene, 1-butene and 2-butene, are oligomerized in the presence of a catalyst prepared by reacting tungsten hexafluoride and water. The synthetic fluid oligomer products, including certain novel products, predominate in those fractions which are suitable, particularly after hydrogenation, for use as functional fluids.

DETAILED DESCRIPTION OF THE INVENTION

A number of processes have been proposed for the oligomerization of alpha-olefins to form synthetic fluid materials and a few have been used commercially. The olefin of choice is generally 1-decene since both the trimer and tetramer are excellent lubricants, and the catalyst of choice is boron trifluoride since it results in the preparation of a high proportion of the trimer and tetramer of 1-decene when used with suitable cocatalytic materials. Processes of this type are described in U.S. Pat. Nos. 3,149,178; 3,382,291; 3,763,244; 3,769,363; 3,780,128; and 3,997,621. However, no suitable prior art oligomerization process is known to us which produces high yields of oligomer fractions for use as functional fluids from propylene, 1-butene or 2-butene, or from mixtures of these olefins. We have found that boron trifluoride is essentially catalytically inactive in attempting to oligomerize these lower olefins at atmospheric pressure. On the other hand we have found that aluminum trichloride actively catalyzes these lower 1-olefins predominantly to the dimer and trimer, which oligomer product can be used in gasoline formulations. Internal olefins and in particular 2-butene are known to be difficult to oligomerize.

We have surprisingly discovered a process for oligomerizing lower olefins such as propylene and 1-butene in high yield to those liquid oligomer fractions which are suitable for use as functional fluids. More surprisingly our novel process also oligomerizes 2-butene to oligomer fractions suitable for use as functional fluids in high yield. And most surprisingly we have discovered that these oligomerization reactions can be carried out at atmospheric pressure. These lower olefins can be individually oligomerized or they can be co-oligomerized by our process. We have also discovered as a part of our invention that our process can be used to oligomerize or co-oligomerize higher 1-olefins either separately or jointly with these lower olefins to produce useful synthetic fluids. Therefore, we find that our novel process relates to the oligomerization or co-oligomerization of one or more olefins selected from 2-butene and 1-olefins having from three to about twelve carbon atoms as defined by the formula $CH_2=CH-R$ wherein R is alkyl having from one to about ten carbon atoms.

The catalyst used in our process is the reaction product of tungsten hexafluoride and water. It is prepared by reacting tungsten hexafluoride and water, either externally or in situ, using a critical ratio of the two components. We have found that oligomerization does not occur when water is excluded both from the catalyst and the reaction system. Since this catalyst is soluble in the hydrocarbon reaction medium, a homogeneous reaction system is formed. In carrying out the oligomerization reaction by the preferred procedure of metering in the olefin into the liquid reaction mixture containing the catalyst, we have found that after a period of time the reaction rate decreases. When such decrease in the reaction rate occurs, we have determined that the reaction can be renewed by adding an appropriate amount of additional water. We believe that the water tied up in the catalyst may gradually be withdrawn from the catalyst during the reaction causing a decrease in the activity of the catalyst, which activity is then regenerated by adding the additional quantity of water. The reaction can go through a series of these rate decrease and catalyst regeneration cycles involving water depletion and renewal before the catalyst eventually resists regeneration by water addition.

We have found that superior results can be obtained in converting the olefin to oligomer product and in obtaining selectivity to the desired oligomer fractions when the mol ratio of tungsten hexafluoride to water at the beginning of the reaction and at the initiation of each subsequent cycle is controlled within specified limits. Thus, we find that for suitable results the catalyst should be prepared by using at least about 0.05 mol of water per mol of tungsten hexafluoride up to a maximum of about 0.5 mol of water per mol of tungsten hexafluoride. However, we can broadly define the relative amounts of tungsten hexafluoride and water that can be used as being a catalytically effective ratio of these two catalyst components. We prefer a mol ratio of tungsten hexafluoride to water at the beginning of each cycle of between about 3:1 and about 10:1 and have determined that a ratio of about 4:1 to about 5:1 is most preferred. In the concluding claims the mol ratio of these catalyst components is the mol ratio that is used at the initiation of the oligomerization reaction and each subsequent cycle. Since it is known that tungsten hexafluoride hydrolyzes completely at a mol ratio of 1:4, a substantial excess of water can be used during product recovery to irreversibly decompose and deactivate the tungsten hexafluoride following the conclusion of the oligomerization. Sufficient catalyst is utilized in the oligomerization reaction to accomplish the oligomerization of the desired quantity of olefin before the catalyst eventually becomes inactive, which amount is the catalytically effective quantity of catalyst. A large excess of the catalyst can be used, but this would, in general, not be desirable unless the tungsten hexafluoride is eventually recovered, such as by a vaporization procedure.

The oligomerization is desirably carried out in the liquid phase in a suitable inert liquid solvent such as a paraffinic hydrocarbon or a halogenated paraffinic hydrocarbon. The amount of the inert solvent that can conveniently be used is from about zero percent up to about 75 weight percent of the total oligomerization reaction system. However, we prefer that the solvent comprise between about 5 and about 50 weight percent of the total reaction system. Suitable solvents include the liquid alkanes and cycloalkanes having between about five and about 60 carbon atoms, such as pentane, hexane, heptane, octane, cyclopentane, cyclohexane, or, alternatively, the unhydrogenated or hydrogenated oligomer reaction product or fraction thereof, and the like. Also useful as solvents are the halogenated alkanes having from one to about 20 carbon atoms, such as carbon tetrachloride, chloroform, ethylene dichloride, and the like. Aromatic compounds such as benzene are not inert since they are alkylated by the olefin reactant. Certain oxygen-containing organic compounds such as methanol, ethanol, acetone, dioxane and triglyme are not useful because they have been found to deactivate the catalyst. It is desirable that the boiling point of the solvent at 760 mm. Hg. be between 30° and about 500° C. When the catalyst is made up as a solution in the solvent, it is preferred that the catalyst comprise between about 10 and about 50 weight percent of the solution, but catalyst solutions outside this range are also useful.

A solvent is desirably selected having a boiling point which is well above the reaction temperature so that the liquid state can be easily maintained in the reactor. At the same time the boiling point is also desirably selected which is sufficiently different from any reactant or oligomer product to permit simple distillative separation of the various constituents in the reaction product. In general, an inert solvent is used in the reaction, although it is also possible to use an excess of the olefin as a solvent, such as by carrying out the oligomerization as a simple batch reaction. But this procedure is generally avoided since using excess olefin as the reaction medium makes it more difficult both to carry out the reaction and to control the reaction temperature. The solvent not only functions as a medium for dissolving both the reactants and the catalyst but it also desirably serves as a heat sink to help control the temperature of the exothermic oligomerization reaction.

The reaction can suitably be carried out at a temperature between about 2° C. and about 100° C., but it is preferably carried out at a temperature between about 15° C. and about 70° C. Since tungsten hexafluoride solidifies at about 2° C., this temperature is selected as a convenient minimum operating temperature. The upper limit of about 100° C. is selected because the catalyst begins to decompose above this temperature. The pressure in the reactor is not critical. A particular advantage of the present process is that it can be carried out at atmospheric pressure, in fact, the most preferred pressure range is about one to about five atmospheres. However, the reaction can be carried out at subatmospheric pressures as well as at elevated pressures including pressures up to about 1,000 psia. and higher.

In carrying out the reaction we prefer to make the catalyst in situ by separately adding suitable quantities of the tungsten hexafluoride and the water to the reaction solvent, however, it can also be prepared ex situ and then introduced into the reactor. The olefin is then added incrementally such as by metering it into the reactor at a rate to maintain the desired temperature for the exothermic reaction. Supplemental heating or cooling of the reaction liquid may also be desirable. We have also found as a variant of this procedure that a minor portion of the olefin reactant can first be added to the reaction solvent followed by the tungsten hexafluoride and then the water. Perceptible oligomerization does not take place until the water is added. The reaction is then completed by metering in the remaining portion of the olefin to the reaction liquid. The greater the concentration of the catalyst in the solution the greater the reaction rate. Therefore, although the oligomerization will take place, albeit slowly, in extremely dilute catalyst solutions, it is preferred that sufficient catalyst be used to provide a suitable reaction rate at the reaction conditions being utilized, taking notice that the catalyst is diluted as the olefin is metered into the reaction solution.

Since the tungsten hexafluoride is soluble in paraffinic hydrocarbon solvents, it is most conveniently utilized as a solution in the same solvent that will be used as the reaction medium so that the liquid tungsten hexafluoride solution can be conveniently handled and added to the reaction zone in appropriate amounts as required. However, gaseous tungsten hexafluoride is also suitable and can be dissolved in situ by injecting it directly into the reactor liquid. Although there is an indication that a minor amount of the olefin may become incorporated by reaction into the catalyst material, the catalyst is conveniently described herein as the chemical combination of tungsten hexafluoride and water, which reaction has clearly been observed to occur.

The expressions synthetic fluids, synthetic oils and functional fluids are used herein with reference to those synthetic hydrocarbon fractions which have between about 20 and about 60 carbon atoms per molecule, therefore, the term oligomer is used herein with reference to products having up to about 60 carbon atoms. This carbon number range corresponds to a molecular weight range of between about 280 and about 840. Useful functional fluids which may be obtained by our process include, for example, but are not necessarily restricted to lubricating oils, hydraulic fluids, transmission fluids, transformer fluids, pesticidal oils, vehicles for pesticides and herbicides, and the like. The preferred lubricating oil range from which automobile engine lubricating oils are desirably prepared are those hydrocarbon fractions which have between about 28 and 44 carbon atoms per molecule.

The carbon number or molecular weight distribution of the product can be controlled to some degree by controlling the reaction temperature and the time of reaction. The higher the temperature and the shorter the reaction time the lower the average molecular weight of the oligomer product. Therefore, if a lower average product molecular weight is desired, the oligomerization is carried out at a higher temperature within the specified range. The total reaction time can also be reduced but this may also reduce the amount of the olefin that is reacted. The lower oligomer fractions, such as those containing up to about 19 carbon atoms or higher, as desired, can be separated from the reaction product and recycled to the reactor for reaction with the feed olefin to build up the molecular weight to a desired level. On the other hand, if there is no current use for an oligomer fraction having a high molecular weight, such as the fraction having more than 44 carbon atoms per molecule, the high molecular weight product fraction may represent a process loss. Process efficiency can therefore be effected by operating at conditions for a somewhat lower average molecular weight than is actually desired and recycling the light ends to convert them to a useful product.

Separation of the oligomer product by fractional distillation can be conveniently accomplished up to about 36 to about 44 carbon atoms with separation by distillation becoming increasingly more difficult the higher the carbon number. Therefore, the still bottoms containing more than about 36 to 44 carbon atoms is generally recovered as one product. This high-molecular weight still bottoms product can either be utilized as a functional fluid, such as a lubricant in specific applications requiring a high viscosity lubricant, or it can be diluted with lower viscosity material to produce a product of moderately high viscosity. When produced in excess, the still bottoms can be cracked into lower molecular weight components or burned as a fuel. This still bottoms product can contain a minor amount of oligomer fractions having more than 60 carbon atoms which will vary in amount depending on the conditions under which the oligomerization reaction is conducted. The oligomer product is generally hydrogenated prior to use to remove olefinic unsaturation and thereby stabilize the product. Conventional hydrogenation procedures and catalyst can be used such as Raney nickel, supported platinum or palladium, and the like at a suitable elevated temperature and pressure.

DESCRIPTION OF PREFERRED EMBODIMENTS

Fuel grade n-heptane which had been dried in a molecular sieve, except where noted, and commercial grade dry olefin were used in the following experiments. The reactors were three-neck round bottom flasks of various sizes equipped with rubber septum, Teflon-coated magnetic stirring bar, thermocouple well, and reflux condenser containing a solid carbon dioxide cold-finger at the upper end. Moderation and control of the reaction temperature were obtained by placing the reactor in a water bath at about 20° C. In most experiments a pale yellow solution of 0.2 to 0.5 g of tungsten hexafluoride per ml of n-heptane was charged to the reactor. In some experiments pure tungsten hexafluoride was charged directly into the reactor. At the completion of the reaction the catalyst was deactivated by agitation with an excess of water. The resulting yellow solid was identified as $WO_3.2H_2O$ by X-ray diffraction. The organic layer was separated and washed with aqueous sodium hydroxide to neutralize the hydrogen fluoride and then washed with water until neutral. The organic product was dried over anhydrous sodium sulfate and the n-heptane was removed by heating under vacuum to yield a colorless to yellow, clear oligomer oil. The carbon number analysis of the oligomer product was obtained by gas chromatography. No dimer was identified in any of the butene oligomer products.

EXAMPLE 1

This experiment illustrates the preparation of the catalyst and its use in the oligomerization of 1-butene. A one liter flask was heated overnight in a vacuum and was purged with nitrogen. A 40 milliliter (ml) portion of n-heptane was charged to the reactor in an 18° C. bath and the stirrer was started. Ten ml of a pale yellow solution of n-heptane containing 2.6 grams (g) of tungsten hexafluoride (9.07 mmols) was added to the reactor. Following this 39 milligrams (mg) of water (2.17 mmols) was charged to the reactor and this reacted with the tungsten hexafluoride to form a reaction product comprising the tungsten hexafluoride and the water in a molar ratio of 4.18:1. The addition of the water into the reactor also caused a slight fog to develop in the previously clear atmosphere about the reactor liquid.

After stirring the catalyst solution for five minutes, a stream of 1-butene was introduced into the reactor until a total of 178 g of 1-butene was added. The exothermic reaction caused the temperature of the reactor contents to rise giving an average temperature of 26° C. and a high of 34° C. over a total reaction time of 285 minutes. The catalyst was deactivated and 147 g of trimer and higher oligomer product was recovered, representing a conversion of 83 percent. The amount of trimer and tetramer was 1.3 percent, the yield of $C_{20}$ to $C_{36}$ was 45.0 percent and the yield of $C_{40}$ and higher product was 53.7 percent.

EXAMPLE 2

This experiment demonstrates that tungsten hexafluoride is inactive for the oligomerization reaction of 1-butene unless a minute amount of water is reacted with the tungsten hexafluoride. A 100 ml portion of n-heptane was charged into a 500 ml flask. About 1.5 g of liquid tungsten hexafluoride was injected into the reactor from a cylinder and 81 g of 1-butene was bubbled into the reactor. There was no temperature rise over a period of 215 minutes and no reaction was observed. At this time 10 drops (about 0.01 g) of water were added resulting in a mol ratio of tungsten hexafluoride to water of about 9:1. After a 20 second delay, initiation of the oligomerization reaction occurred and the temperature quickly rose to 58° C. The addition of 1-butene was continued over a 90-minute period to an overall total of 101 g. Analysis of the 96.5 g oligomer product showed 0.9 weight percent in the $C_{12}$ fraction, 2.8 percent $C_{16}$, 4.9 percent $C_{20}$, 6.6 percent $C_{24}$, 9.0 percent $C_{28}$, 18 percent $C_{32}$ and 57.8 greater than $C_{32}$.

EXAMPLES 3-7

These experiments were conducted using different quantities of water to determine the effect of different tungsten hexafluoride to water mol ratios. In these experiments 40 ml of dried n-heptane was added to a 125 ml flask in an 18° C. bath and this was saturated with 1-butene (about 12.5 g). The heat of solution caused the temperature to rise about 28° C. When the solution was saturated and the temperature had dropped to about 18° C., the pale yellow solution of 2.6 g of tungsten hexafluoride in 10 ml of n-heptane was charged to the reactor. The clear, colorless solution in the reactor turned bright yellow on this addition but there was no temperature rise. A specific amount of water was added causing the yellow color to turn dark brown and resulting in the appearance of a white fog above the solution. After about three minutes the temperature started to rise reaching a maximum of about 50°-65° C. in about 6 to 18 minutes. The temperature was permitted to fall to the desired operating range of about 18° C. and then the 1-butene was pumped into the solution at a rate to maintain the reaction temperature. When reaction stopped as indicated by a decreasing temperature, the introduction of the 1-butene was stopped. Specific operating details and analysis of the oligomer products are set out in Table I in which conversion is to oligomer product having 12 or more carbon atoms.

TABLE I

| Example | 3 | 4 | 5 | 6 | 7 |
|---|---|---|---|---|---|
| 1-butene, g | 26.6 | 52.2 | 57.4 | 53.5 | 53.0 |
| Water, g | .16 | .054 | .04 | .03 | .02 |
| $WF_6:H_2O$, (mol) | 1:1 | 2.9:1 | 3.9:1 | 5.2:1 | 7.9:1 |
| Time, min. | 53 | 87 | 120 | 85 | 118 |
| Max. Temp. °C. | 50 | 62 | 62 | 63 | 31 |
| Av. Temp. °C. | 27 | 24 | 30 | 23 | 23 |
| Conversion, % | 32 | 76 | 84 | 75 | 71 |
| Oligomer, wt. % | | | | | |
| $C_{12}$ | 4 | .03 | 0.2 | .3 | .4 |
| $C_{16}$ | 13 | 3.6 | 2.6 | 2.1 | 4.2 |
| $C_{20}$ | 22 | 5.7 | 7.3 | 6.2 | 6.5 |
| $C_{24}+$ | 61 | 90.6 | 89.9 | 91.4 | 88.9 |

EXAMPLE 8

In this experiment the periodic need to add water to the reactor during the oligomerization process to regenerate the catalyst was studied. A 40 ml quantity of n-heptane was introduced into a 500 ml flask at 20° C. which was then saturated with about 12 g of 1-butene. This was followed by 3.1 g of tungsten hexafluoride in 5 ml of n-heptane. A 15 microliter (0.015 g) quantity of water was injected into the solution and the bright yellow solution turned dark brown as before and the temperature rose to about 20° C. in about 16 minutes. 1-Butene was pumped into the reactor until the temperature dropped to the bath temperature of 19° C. A total of 62 g of 1-butene not including the initial addition, was introduced over a 41 minute period. At this point a second 0.015 g portion of water was introduced into the reactor and 1-butene was pumped into the reactor as the reaction renewed. This was continued for 26 minutes until the reaction again stopped after 41 g of 1-butene had been added. This renewal process was repeated through a total of six cycles in which a total of 0.09 g of water was added in equal quantities and 272 g of 1-butene had been introduced into the reactor over 233 minutes. The overall conversion to oligomer was 90 percent.

EXAMPLE 9

This experiment involved the repeated addition of water to renew the reaction after the reaction had stopped in a manner similar to the preceding example. A 200 ml portion of n-heptane was charged to a 2,000 ml flask and 1-butene was bubbled in to saturation. A 20.7 ml portion of a catalyst solution containing 6.5 g of tungsten hexafluoride was injected into the solution followed by 0.09 g of water. After the temperature had stabilized at about 26° C., the 1-butene was injected into the reaction liquid until the reaction stopped. A series of three more sequential water additions amounting to 0.06, 0.03 and 0.09, respectively, were made to renew the reaction after it had stopped resulting in a total of 0.270 g of water, and a total of 529 g of 1-butene having been added for an overall reaction time of 435 minutes. Analysis of the product oligomer showed an overall conversion of 86 percent to 12 carbon and higher product, distributed one percent to $C_{12}$ oligomer, two percent to $C_{16}$, three percent to $C_{20}$, 32 percent to $C_{24}$ through $C_{32}$ and 61 percent greater than $C_{32}$.

EXAMPLE 10

Another experiment was carried out following the general procedure set out in Example 9. This experiment was carried out in a 5,000 ml flask and involved 400 ml of n-heptane, a total of 13.9 g of tungsten hexafluoride, a total of 0.49 g of water, a total reaction time of 540 minutes at an average reaction temperature of 30°–40° C. wherein a total of 1,132 g of 1-butene was reacted at 88 percent conversion to 12 carbon oligomer produce and higher. This oligomer product analyzed as one percent to $C_{12}$ oligomer, four percent to $C_{16}$, 12 percent to $C_{20}$, 17 percent to $C_{24}$, 20 percent to $C_{28}$, 18 percent to $C_{32}$ and 28 percent higher than $C_{32}$. This oligomer product was distilled at 0.3 mm of mercury and 295 g of the vapor having a boiling range between 52° and 154° C. was collected for use as a recycle feed in the following experiment.

EXAMPLE 11

This experiment demonstrated the use of a light ends recycle feed used in conjunction with fresh olefin feed to the reactor. In this reaction 18 g of recycle stock which analyzed three percent $C_{12}$ oligomer, 14 percent $C_{16}$, 28 percent $C_{20}$, and 55 percent $C_{24}$ were combined with 15 g of fresh 1-butene in 20 ml n-heptane. A total of 2.1 g of tungsten hexafluoride and 0.04 g of water were used and an additional 51 g of 1-butene was injected into the reactor during reaction for a total reaction time of 195 minutes at an average reaction temperature of 35° C. Analysis of the oligomer product showed a 74 percent conversion to 12 carbon and higher oligomer product analyzing 0.8 percent $C_{12}$ oligomer, 1.6 percent $C_{16}$, 6 percent $C_{20}$, 14 percent $C_{24}$, 13 percent $C_{28}$, 14 percent $C_{32}$, 14 percent $C_{36}$ and 36.6 percent greater than $C_{36}$.

EXAMPLE 12

In this experiment the oligomer product obtained from 1-butene was hydrogenated and the viscosity properties were obtained. Three runs were carried out at similar conditions using a total of 1,800 g of 1-butene to obtain 1,585 g of oligomer product having 12 carbon atoms and higher. In these three runs the overall mol ratios of tungsten hexafluoride to water which were reacted to form the catalyst were 4:1, 4:1 and 3:15, respectively. The three runs were separately hydrogenated using platinum oxide catalyst and 50 psig of hydrogen at 100° C. The combined hydrogenated product of runs 1 and 2 was distilled and 463 g of a cut out of a total of 1,211 g was obtained having a boiling point of 161°–231° C. at a pressure of about 0.45 mm Hg. This cut analyzed 23.5 percent $C_{28}$, 25.3 percent $C_{32}$ and 51.1 percent $C_{36}$. The third run was distilled and 157 g of a cut was obtained boiling at 161°–233° C. at a pressure of about 0.25 mm Hg out of a total of 315 g. This cut analyzed 26.7 percent $C_{28}$ and 73.2 percent $C_{32}$ and $C_{36}$. These two cuts were combined to form 620 g of a material which had a 0° F. viscosity of 3,872 centistokes (cs), a 100° F. viscosity of 42.48 cs, a 210° F. viscosity of 5.55 cs, a viscosity index of 63 and a pour point of −50° F.

EXAMPLE 13

A 125 ml flask was charged with 25 ml of n-heptane saturated with about 2.5 mg of water at 4.0° C. and to this was added 11.2 g of cis-2-butene. Twenty ml of n-heptane containing one gram of tungsten hexafluoride was added without reaction. A 0.1 g portion of water was added without reaction. After an unmeasured quantity of tungsten hexafluoride gas was injected into the reactor, reaction as initiated. The reaction time was 120 minutes at an average temperature of 15° C. An oligomer product weighing 10.9 grams was recovered which was a 95 percent conversion to oligomer which analyzed 0.5 percent $C_{12}$, 1.8 percent $C_{16}$, 5.3 percent $C_{20}$ and 88.9 percent higher than $C_{20}$.

EXAMPLE 14

Forty milliliters of n-heptane were introduced into a 125 ml flask. About ten grams of 1-butene are added to saturate the solution. A n-heptane solution containing 1.2 g of tungsten hexafluoride is added followed by 17 mg of water causing the temperature to rise to 33° C. A 25 g mixture containing 63.5 percent 1-butene and 36.5 percent of a cis- and trans-mixture of 2-butene was pumped in over a 23 minute period. The reaction was continued for 15 minutes to completion and 30 g of the oligomer product was recovered after catalyst removal. This product analyzed one percent $C_{12}$ oligomer, 7 percent $C_{16}$, 16 percent $C_{20}$, 19 percent $C_{24}$, 18 percent $C_{28}$, 15 percent $C_{32}$, and 24 percent greater than $C_{32}$.

EXAMPLE 15

In this experiment propylene was oligomerized in three separate runs to obtain a sufficient quantity of the desired oligomer product. In a typical run the oligomer was made in a 2,000 ml flask using an initial 100 ml quantity of n-heptane which was saturated with about 30 g of propylene before 20 ml of n-heptane containing 10 g of tungsten hexafluoride and 150 mg of water were added. Propylene was pumped into the reactor and periodic additions of water and/or tungsten hexafluoride were made as required for the reaction. The three runs were fed a total of 1,022 g of propylene producing a total of 792 g of oligomer product using 92 g of tungsten hexafluoride and 1,935 mg of water. The oligomer product was hydrogenated in two batches using a commercial nickel hydrogenation catalyst and the total hydrogenated product was then distilled to obtain four distillate cuts and a bottoms fraction. Cut 1 amounting to eight percent of the product contained $C_{12}$ to $C_{21}$ fractions and had a 100° F. viscosity of 4.23 cs and a 210° F. viscosity of 1.44 cs. Cut 2 at nine percent of the product contained $C_{24}$ and $C_{27}$ fractions and showed a 100° F. viscosity of 14.3 cs and a 210° F. viscosity of 2.89 cs. Cut 3 also at eight percent contained $C_{27}$ and $C_{30}$ fractions and showed a 100° F. viscosity of 31.0 cs and a 210° F. viscosity of 4.39 cs. Cut 4 at 31 percent contained $C_{27}$ to $C_{33}$ fractions and showed a 100° F. viscosity of 81.2 cs and a 210° F. viscosity of 7.50 cs. The bottoms portion amounting to 44 percent comprised fractions higher than 30 carbon atoms and showed a 100° F. viscosity of 995 cs and a 210° F. viscosity of 32.7 cs.

EXAMPLE 16

A 1,000 ml flask was charged with 100 g of 1-decene, heated to 48° C., and followed by six grams of tungsten hexafluoride in n-heptane. When 45 mg of water were added, the temperature quickly rose from 48° C. to 105° C. for about two minutes and then it decreased to about 50° C. Another 45 mg quantity of water was injected into the reactor and an additional 400 g of 1-decene were added over 33 minutes at an average temperature of 50° C. After completion of the reaction, the product was hydrogenated and the resulting 462 g were distilled to separate oligomer from light ends. Analysis showed 31 percent 1-decene, 15 percent dimer, 18 percent timer, 12 percent tetramer and 24 percent higher than tetramer.

EXAMPLE 17

Forty milliliters of n-heptane were charged to a 500 ml flask and this was saturated with about ten grams of propylene. A n-heptane solution containing about two grams of tungsten fexafluoride was introduced. After 45 mg of water were injected into the reactor, the temperature rapidly rose from 18° C. to 35° C. Propylene was added over 68 minutes giving a total propylene addition of 84 g up until that point. The propylene was stopped and 70 g of 1-decene were added dropwise over five minutes. The temperature was raised to 40° C. and the reaction proceeded for 30 minutes. At this point 30 mg of water were added and then propylene was added for 80 minutes. At this time 15 mg of water and one gram of tungsten hexafluoride in n-heptane were added and the propylene addition continued for one hour. Another one gram addition of tungsten hexafluoride was made and the propylene addition was continues for 40 minutes until an overall total of 168 g of propylene had been added. After the catalyst had been killed, the 169 g oligomer product was hydrogenated and distilled. The 116 g of bottoms product containing 28 carbon and higher oligomer fractions had a 100° F. viscosity of 104 cs, a 210° F. viscosity of 10.5 cs, a viscosity index of 90 and a pour point of $-35°$ F., while the 53 g of overhead material was oligomer material having more than ten and less than 28 carbon atoms.

EXAMPLE 18

The procedures and quantities in this experiment were almost identical to the preceding example except that 1-butene was used instead of propylene. A total of 168 g of 1-butene and 70 g of 1-decene were reacted using a total of three grams of tungsten hexafluoride and 90 mg of water at an average reaction temperature of 35°–45° C. for an overall reaction time of 300 minutes. The oligomer product weighed 196 g. A second run was carried out almost identically except that 75 mg of water were used and the overall reaction was carried out for 170 minutes, producing 161 g of oligomer product. The product of both runs was combined, then hydrogenated and distilled. Of the 324 g of hydrogenated product that were distilled, 248 g ended up as a 28 carbon and higher bottoms portion having a 100° F. viscosity of 71.0 cs, a 210° F. viscosity of 8.49 cs, a viscosity index of 98 and a pour point of $-45°$ F.; and 61 g were an overhead oligomer product having more than 10 and less than 28 carbon atoms.

EXAMPLE 19

Another copolymer of 1-butene and 1-decene was prepared using a 1,000 ml flask into which 40 ml of n-heptane was charged. A total quantity of 13.8 g of tungsten hexafluoride and 253 mg of water were added to the reactor in increments and a mixture containing 198 g of 1-butene and 150 g of 1-decene was metered into the reaction liquid. The overall reaction time was 390 minutes at a reaction temperature of 40° to 50° C. The catalyst was killed and the oligomer product was hydrogenated and distilled. The 201 g of distillation bottoms containing the 28 carbon and higher fractions had a 100° F. viscosity of 57.4 cs, a 210° F. viscosity of 7.73 cs, a viscosity index of 108 and a pour point less than $-65°$ F.

Certain combinations of the hydrogenated oligomers can be used against orchard pests, such as mites, scale, various lepidoptera and the like. They can be sprayed, preferably as a dilute aqueous emulsion, on dormant or leafed deciduous trees or on citrus trees against the adult pest or against its eggs or larva. Separate pesticidal constituents such as insecticides, fungicides and the like can be included where appropriate. These orchard spray oils are desirably prepared by the oligomerization of propylene, 1-butene, 2-butene or mixtures thereof with up to 50 weight percent 1-pentene and 1-hexene. These pesticidal compositions are the oligomer mixtures of these olefins which have between about 20 and about 32 carbon atoms and most desirably are the oligomers of 1-butene, 2-butene and mixtures of 1-butene and 2-butene. These oligomer mixtures are characterized by an absence of aromaticity and after hydrogenation show an unsulfonated residue of at least about 95 percent or higher by ASTM D483. They are also characterized by low pour points having a maximum of about −20° F., preferably a maximum pour point of about −40° F., and by a relatively narrow boiling range characterized by a maximum of 80° F. (26° C.) between the 10 percent and 90 percent point with the 50 percent point being between 425° and 450° F. (218.5° and 232° C.).

EXAMPLE 20

A total of 1,756 g of an oligomer product was made in six runs by the general procedures described in Example 13 from a total of 4,010 g of a mixed butanebutene feed. The feed contained 32.7 percent 1-butene, 25.8 percent trans-2-butene and 7.6 percent cis-2-butene. Due to the relatively high content of the unreactive paraffins, periodic venting was necessary during the oligomerization reaction to reduce the accumulation of inert gases resulting in an overall conversion of 66 percent. The product was hydrogenated over nickel to produce 1,685 g of a synthetic oil. Distillation of this hydrogenated product resulted in a center 529 g fraction having a 50 percent boiling point of about 435° F. with about 80° F. between the ten and ninety percent boiling points. A two percent aqueous emulsion of this hydrogenated oligomer prepared with a suitable emulsifying agent effectively kills eggs of the San Jose scale overwintering in apple trees when applied as a spray to the trees during the dormant season.

It is to be understood that the above disclosure is by way of specific example and that numerous modifications and variations are available to those of ordinary skill in the art without departing from the true spirit and scope of the invention.

We claim:

1. A method for preparing a synthetic hydrocarbon fluid which comprises contacting an olefin reactant selected from 2-butene, an olefin having the formula $CH_2=CH-R$ wherein R is alkyl having from one to about ten carbon atoms, and mixtures thereof and a catalytic amount of the reaction product of tungsten hexafluoride and water wherein tungsten hexafluoride and water are reacted in a mol ratio of between about 2:1 and about 20:1.

2. A method for preparing a synthetic hydrocarbon fluid in accordance with claim 1 in which the reaction temperature is between about 2° C. and about 100° C.

3. A method for preparing a synthetic hydrocarbon fluid in accordance with claim 1 in which the olefin reactant comprises 1-butene.

4. A method for preparing a synthetic hydrocarbon fluid in accordance with claim 1 in which the olefin reaction comprises 2-butene.

5. A method for preparing a synthetic hydrocarbon fluid in accordance with claim 1 in which the olefin reactant comprises a mixture of 1-butene and 2-butene.

6. A method for preparing a synthetic hydrocarbon fluid in accordance with claim 1 in which the olefin reactant comprises propylene.

7. A method for preparing a synthetic hydrocarbon fluid in accordance with claims 3, 4, 5 or 6 in which the olefin reactant comprises said lower olefin and from about 20 to about 80 mol percent of one or more olefins wherein R is alkyl having from about four to about 10 carbon atoms.

8. A method for preparing a synthetic hydrocarbon fluid in accordance with claim 1 in which tungsten hexafluoride and water are reacted in a mol ratio of between about 3:1 and about 10:1.

9. A method for preparing a synthetic hydrocarbon fluid in accordance with claim 1 in which the reaction mixture is between about 15° C. and about 70° C.

10. A method for preparing a synthetic hydrocarbon fluid in accordance with claim 1 in which the olefin reactant additionally comprises a recycle light end having at least 12 carbon atoms and no greater than about 24 carbon atoms.

11. A method for preparing a synthetic hydrocarbon fluid in accordance with claim 1 in which tungsten hexafluoride and water are reacted in a mol ratio of between about 4:1 and about 5:1.

12. A method for preparing a synthetic hydrocarbon fluid in accordance with claim 1 in which the oligomer product predominates in fractions having between about 20 and about 60 carbon atoms.

13. A method for preparing a synthetic hydrocarbon fluid in accordance with claim 1 in which the oligomer product predominates in fractions having between about 28 and about 44 carbom atoms.

14. A method for preparing a synthetic hydrocarbon fluid in accordance with claim 1 in which the oligomer product predominates in fractions having between about 20 and about 32 carbon atoms.

15. A method for preparing a synthetic hydrocarbon fluid in accordance with claim 1 in which the oligomer product is hyrogenated.

16. A method for preparing a synthetic hydrocarbon fluid in accordance with claim 1 in which the reaction mixture comprises an inert liquid organic solvent.

17. A method for preparing a synthetic hydrocarbon fluid in accordance with claim 16 in which said solvent is selected from alkanes and cycloalkanes having from about five to about 60 carbon atoms and halogenated alkanes having from one to about 20 carbon atoms.

18. A method for preparing a synthetic hydrocarbon fluid in accordance with claim 16 in which said solvent comprises from about five to about 50 weight percent of said reaction mixture.

19. A synthetic hydrocarbon fluid comprising the hydrogenated oligomer mixture containing between about 20 and about 32 carbon atoms per molecule and prepared by the oligomerization of a 1-olefin selected from propylene, 1-butene, 2-butene, and mixtures thereof with up to about 50 mol percent of 1-olefin selected from 1-pentene, 1-hexene or a mixture thereof.

20. A synthetic hydrocarbon fluid in accordance with claim 19 in which said hydrogenated oligomer mixture is prepared by the oligomerization of 1-butene, 2-butene or a mixture thereof.

21. A synthetic hydrocarbon fluid in accordance with claim 19 in which said hydrogenated oligomer mixture has an unsulfonated residue of at least about 95 percent, a maximum pour point of about −40° F., a distillation midpoint of between about 425 and about 450° F. and a maximum of 80° F. between the 10 percent and 90 percent distillation points.

* * * * *